United States Patent
Zhao et al.

(10) Patent No.: US 12,394,187 B2
(45) Date of Patent: Aug. 19, 2025

(54) SYNTHESIS OF MEDICAL IMAGES OF BRAIN TUMORS USING 3D-2D GANS

(71) Applicant: Siemens Medical Solutions USA, Inc., Malvern, PA (US)

(72) Inventors: Gengyan Zhao, Plainsboro, NJ (US); Youngjin Yoo, Princeton, NJ (US); Thomas Re, New York, NY (US); Eli Gibson, Plainsboro, NJ (US); Dorin Comaniciu, Princeton, NJ (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 458 days.

(21) Appl. No.: 18/161,186

(22) Filed: Jan. 30, 2023

(65) Prior Publication Data

US 2024/0062523 A1 Feb. 22, 2024

Related U.S. Application Data

(60) Provisional application No. 63/373,122, filed on Aug. 22, 2022.

(51) Int. Cl.
*G06V 10/774* (2022.01)
*G06T 5/50* (2006.01)
(Continued)

(52) U.S. Cl.
CPC ............ *G06V 10/774* (2022.01); *G06T 5/50* (2013.01); *G06T 5/70* (2024.01); *G06T 7/0012* (2013.01);
(Continued)

(58) Field of Classification Search
CPC .... G06V 10/764; G06V 10/774; G06V 10/82; G06V 2201/03; G06T 5/0012;
(Continued)

(56) References Cited

U.S. PATENT DOCUMENTS 10,937,540 B2 * 3/2021 Madani ................. G06N 3/045
2019/0197358 A1 * 6/2019 Madani ................. G06N 3/045
(Continued)

OTHER PUBLICATIONS

Kim et al., "Synthesis of Brain Tumor MR Images for Learning Data Augmentation", arXiv:2003.07526v1, Mar. 18, 2020, pp. 1-15. (Year: 2020).*
(Continued)

*Primary Examiner* — Nay A Maung
*Assistant Examiner* — Jose M Torres

(57) ABSTRACT

Systems and methods for generating synthesized medical images of a tumor are provided. A 3D mask of an anatomical structure generated from a 3D medical image and a 3D image of a plurality of concentric spheres are received. A 3D mask of a tumor is generated based on the 3D mask of the anatomical structure and the 3D image of the plurality of concentric spheres using a first 3D generator network. A 3D intensity map of the tumor is generated based on the 3D mask of the tumor and the 3D image of the plurality of concentric spheres using a second 3D generator network. A 3D synthesized medical image of the tumor is generated based on one or more 2D slices of the 3D intensity map of the tumor and one or more 2D slices of the 3D medical image using a 2D generator network. The 3D synthesized medical image of the tumor is output.

20 Claims, 10 Drawing Sheets

(51) Int. Cl.
G06T 5/70 (2024.01)
G06T 7/00 (2017.01)
G06V 10/764 (2022.01)
G16H 30/40 (2018.01)
G16H 50/50 (2018.01)

(52) U.S. Cl.
CPC ........... *G06V 10/764* (2022.01); *G16H 30/40* (2018.01); *G16H 50/50* (2018.01); *G06T 2200/04* (2013.01); *G06T 2207/20081* (2013.01); *G06T 2207/20084* (2013.01); *G06T 2207/20212* (2013.01); *G06T 2207/30016* (2013.01); *G06T 2207/30096* (2013.01); *G06V 2201/03* (2022.01)

(58) Field of Classification Search
CPC ..... G06T 5/11; G06T 5/50; G06T 5/70; G06T 11/00; G06T 2200/04; G06T 2207/20081; G06T 2207/20084; G06T 2207/20212; G06T 2207/20221; G06T 2207/30016; G06T 2207/30096; G16H 30/40; G16H 40/67; G16H 50/20; G16H 50/50; G16H 50/70
See application file for complete search history.

(56) References Cited

U.S. PATENT DOCUMENTS

| | | | | |
|---|---|---|---|---|
| 2020/0364864 | A1* | 11/2020 | Shanbhag | G06T 11/008 |
| 2021/0327054 | A1* | 10/2021 | Liu | G06T 7/11 |
| 2021/0383537 | A1* | 12/2021 | Chitiboi | G06T 7/11 |
| 2024/0257339 | A1* | 8/2024 | Girardot | G06T 3/40 |
| 2025/0148601 | A1* | 5/2025 | Sofka | G06T 7/0012 |

OTHER PUBLICATIONS

Achrol et al., "Brain metastases", Natural Reviews, Disease Primers, 2019, pp. 1-26.
Fink et al., "Imaging of brain metastases", Surgical Neurology International, 2013, pp. S209-S219.
Patchell et al., "The management of brain metastases", Cancer Treatment Reviews, 2003, pp. 533-540.
Cho et al., "Brain metastasis detection using machine learning: a systematic review and meta-analysis", Neuro-Oncology, 2021, pp. 214-225.
Zhou et al., "Computer-aided Detection of Brain Metastases in T1-weighted MRI for Stereotactic Radiosurgery Using Deep Learning Single-Shot Detectors", Radiology, 2020, pp. 1-19.
Zhou et al., "MetNet: Computer-aided segmentation of brain metastases in post-contrast T1-weighted magnetic resonance imaging", Radiotherapy and Oncology, 2020, pp. 1-8.
Amemiya et al., "Feature-fusion improves MRI single-shot deep learning detection of small brain metastases", Journal of Neuroimaging, 2022, pp. 1-9.
Cao et al., "Automatic detection and segmentation of multiple brain metastases on magnetic resonance image using asymmetric UNet architecture", Physics in Medicine & Biology, 2021, pp. 1-8.
Shin et al., "Medical Image Synthesis for Data Augmentation and Anonymization Using Generative Adversarial Networks", Simulation and Synthesis in Medical Imaging, arXiv: 1807.10225v2, 2018, 11 pgs.
Allah et al., "Classification of Brain MRI Tumor Images Based on Deep Learning PGGAN Augmentation", Diagnostics, 2021, pp. 1-20.
Han et al., "Infinite Brain MR Images: PGGAN-Based Data Augmentation for Tumor Detection", arXiv:1903.12564v1, 2019, 13 pgs.
Deepak et al., "MSG-GAN Based Synthesis of Brain MRI with Meningioma for Data Augmentation", IEEE International Conference on Electronics, 2020, 6 pgs.
Li et al., "TumorGAN: A Multi-Modal Data Augmentation Framework for Brain Tumor Segmentation", Sensors, 2020, pp. 1-16.
Mok et al., "Learning Data Augmentation for Brain Tumor Segmentation with Coarse-to-Fine Generative Adversarial Networks", arXiv:1805.11291v2, 2018, pp. 1-10.
Kim et al., "Synthesis of brain tumor multicontrast MR images for improved data augmentation", Medical Physics, 2021, pp. 2185-2198.
Yoo et al. "Evaluating deep learning methods in detecting and segmenting different sizes of brain metastases on 3D post-contrast T1-weighted images", Journal Medical Imaging, 2021, pp. 037001-1-037001-16.
Liao et al., "A Fast Algorithm for Multilevel Thresholding", Journal of Information Science and Enginering, 2001, pp. 713-727.
Johnson et al., "Perceptual Losses for Real-Time Style Transfer and Super-Resolution", arXiv:1603.08155v1, 2016, pp. 1-18.
Gatys et al., "Image Style Transfer Using Convolutional Neural Networks", IEEE Conference on Computer Vision and Pattern Recognition, 2016, pp. 2414-2423.
Ronneberger et al., "U-net: Convolutional networks for biomedical image segmentation", International Conference on Medical Image Computing and Computer-Assisted Intervention, arXiv:1505.04597v1, 2015, pp. 1-8.

* cited by examiner

US 12,394,187 B2

SYNTHESIS OF MEDICAL IMAGES OF BRAIN TUMORS USING 3D-2D GANS

CROSS-REFERENCE TO RELATED APPLICATIONS

This application claims the benefit of U.S. Provisional Application No. 63/373,122, filed Aug. 22, 2022, the disclosure of which is herein incorporated by reference in its entirety.

STATEMENT REGARDING FEDERALLY SPONSORED RESEARCH OR DEVELOPMENT

This invention was made with government support under grant number R01CA262182 awarded by the National Institutes of Health. The government has certain rights in the invention.

TECHNICAL FIELD

The present invention relates generally to medical image synthesis, and in particular to synthesis of medical images of brain tumors using 3D (three-dimensional)-2D (two-dimensional) GANs (generative adversarial networks).

BACKGROUND

A brain tumor is a mass or growth of abnormal cells in the brain. The brain tumor may be noncancerous (i.e., benign) or cancerous (i.e., malignant), and may begin in the brain (i.e., a primary brain tumor) or may spread to the brain (i.e., a metastatic brain tumor). Detection and classification of brain tumors is important due to the high morbidity and mortality rate associated with them.

Recently, machine learning and deep learning based models have been proposed for brain tumor classification, segmentation, and detection to facilitate diagnosis and treatment. Such machine learning and deep learning based models are data driven such that their performance and robustness are highly dependent upon the size, quality, and diversity of the training data. However, collecting sufficiently large amounts of such training data is both costly and time-consuming.

BRIEF SUMMARY OF THE INVENTION

In accordance with one or more embodiments, systems and methods for generating synthesized medical images of a tumor are provided. A 3D mask of an anatomical structure generated from a 3D medical image and a 3D image of a plurality of concentric spheres are received. A 3D mask of a tumor is generated based on the 3D mask of the anatomical structure and the 3D image of the plurality of concentric spheres using a first 3D generator network. A 3D intensity map of the tumor is generated based on the 3D mask of the tumor and the 3D image of the plurality of concentric spheres using a second 3D generator network. A 3D synthesized medical image of the tumor is generated based on one or more 2D slices of the 3D intensity map of the tumor and one or more 2D slices of the 3D medical image using a 2D generator network. The 3D medical image of the tumor is output.

In one embodiment, the tumor in the 3D synthesized medical image is smoothed using a 3D Gaussian kernel. The smoothed tumor is extracted from the 3D synthesized medical image. The extracted smoothed tumor is blended with the 3D medical image. The contrast of the extracted smoothed tumor is adjusted.

In one embodiment, one or more of the first 3D generator network, the second 3D generator network, or the 2D generator network are trained based on at least one of 3D training images of a plurality of concentric spheres and 3D and 2D training intensity maps of a tumor. The 3D training images of the plurality of concentric spheres and the 3D and 2D training intensity maps of the tumor are generated by receiving a 3D training image of the tumor and a 3D training mask of the tumor. Multi-Otsu thresholding is applied to classify voxels of the 3D training image within the tumor identified in the 3D training mask to generate the 3D training intensity maps of the tumor. The 3D training images of the plurality of concentric spheres are generated based on a volume of the voxels in each of the classes in the 3D training intensity map of the tumor. The 2D training intensity map of the tumor is generated by unstacking the 3D training intensity map of the tumor along an axis into 2D slices.

In one embodiment, the 2D generator network is trained with adversarial loss using a 2D discriminator network. In one embodiment, the 2D generator network is trained with a 2D perceptual loss. In one embodiment, the 2D generator network is trained with a 2D L1 loss.

In one embodiment, the anatomical structure is a brain of a patient or a healthy subject. In one embodiment, the plurality of concentric spheres comprises three concentric spheres.

In one embodiment, a machine learning based network is trained for performing a medical imaging analysis task based on the 3D synthesized medical image of the tumor.

These and other advantages of the invention will be apparent to those of ordinary skill in the art by reference to the following detailed description and the accompanying drawings.

DETAILED DESCRIPTION

The present invention generally relates to methods and systems for synthesis of medical images of brain tumors using a type of 3D (three-dimensional)-2D (two-dimensional) GANs (generative adversarial networks). Embodiments of the present invention are described herein to give a visual understanding of such methods and systems. A digital image is often composed of digital representations of one or more objects (or shapes). The digital representation of an object is often described herein in terms of identifying and manipulating the objects. Such manipulations are virtual manipulations accomplished in the memory or other circuitry/hardware of a computer system. Accordingly, is to be understood that embodiments of the present invention may be performed within a computer system using data stored within the computer system.

Embodiments described herein provide for a GAN based network architecture for synthesizing 3D medical images of brain tumors. The GAN based network architecture comprises a series of 3D generators for generating 3D intermediate representations of brain tumors and a 2D generator for generating 2D synthetic images of brain tumors using the 3D intermediate representations for step-by-step guidance. The 2D synthetic images are stacked to form a 3D synthetic image of the brain tumor. The brain tumors in the final 3D synthetic image is generated with configurable parameters for controlling, for example, the location, size, structure, heterogeneity, and contrast of the synthesized brain tumors. Advantageously, the 3D intermediate representations generated by the 3D generators preserve interslice continuity in all three dimensions, while the final 3D synthetic image is generated by the 2D generator trained using a 2D perceptual loss to ensure that realistic brain tumors are generated with high perceptual quality. The 3D synthesized medical images synthesized in accordance with embodiments described herein may be utilized for, e.g., data augmentation during training machine learning networks for classifying, segmenting, detecting, etc. brain tumors.

Figure 1:
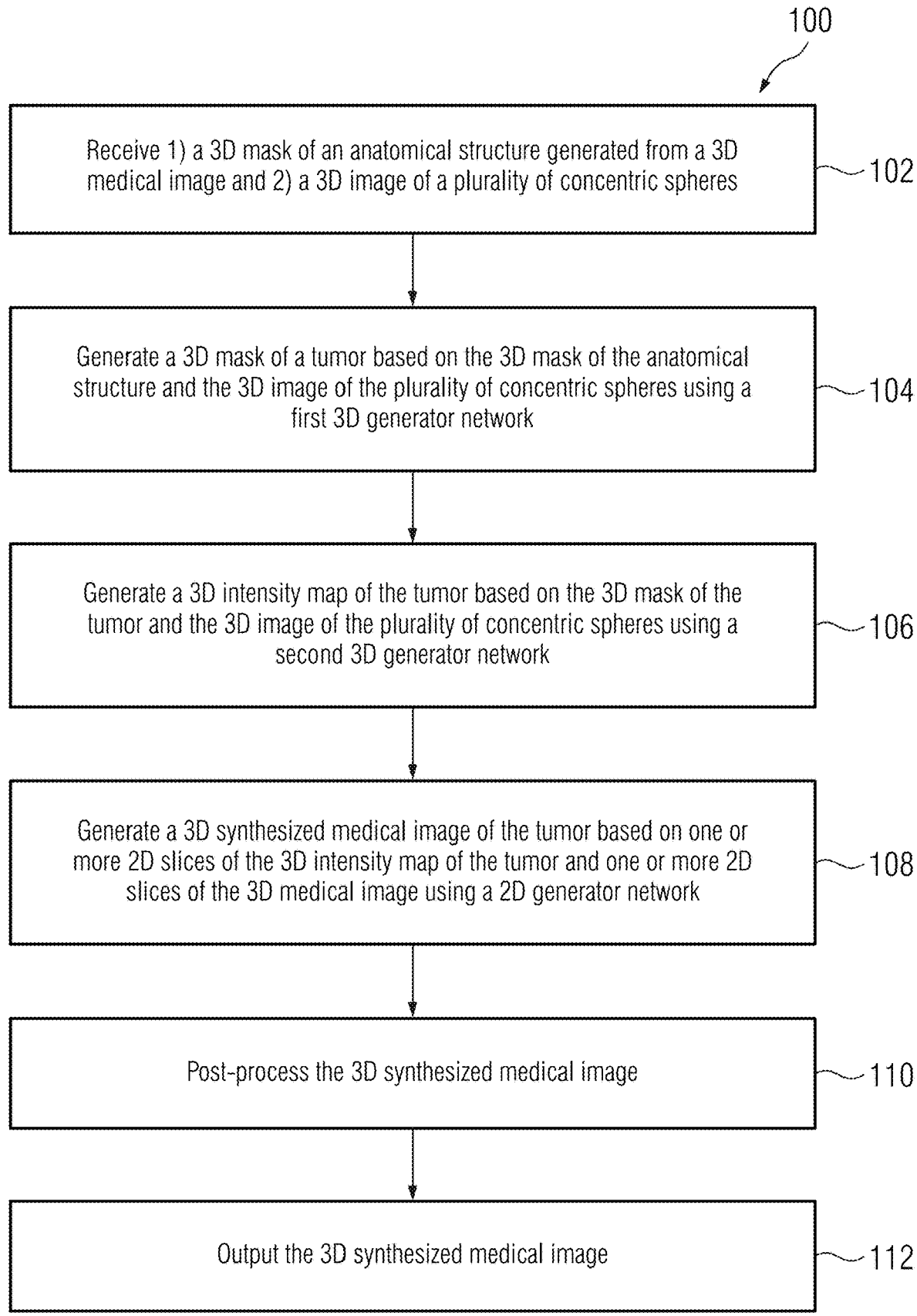
FIG. 1 shows a method for generating synthesized medical images of a tumor, in accordance with one or more embodiments.
Figure 2:
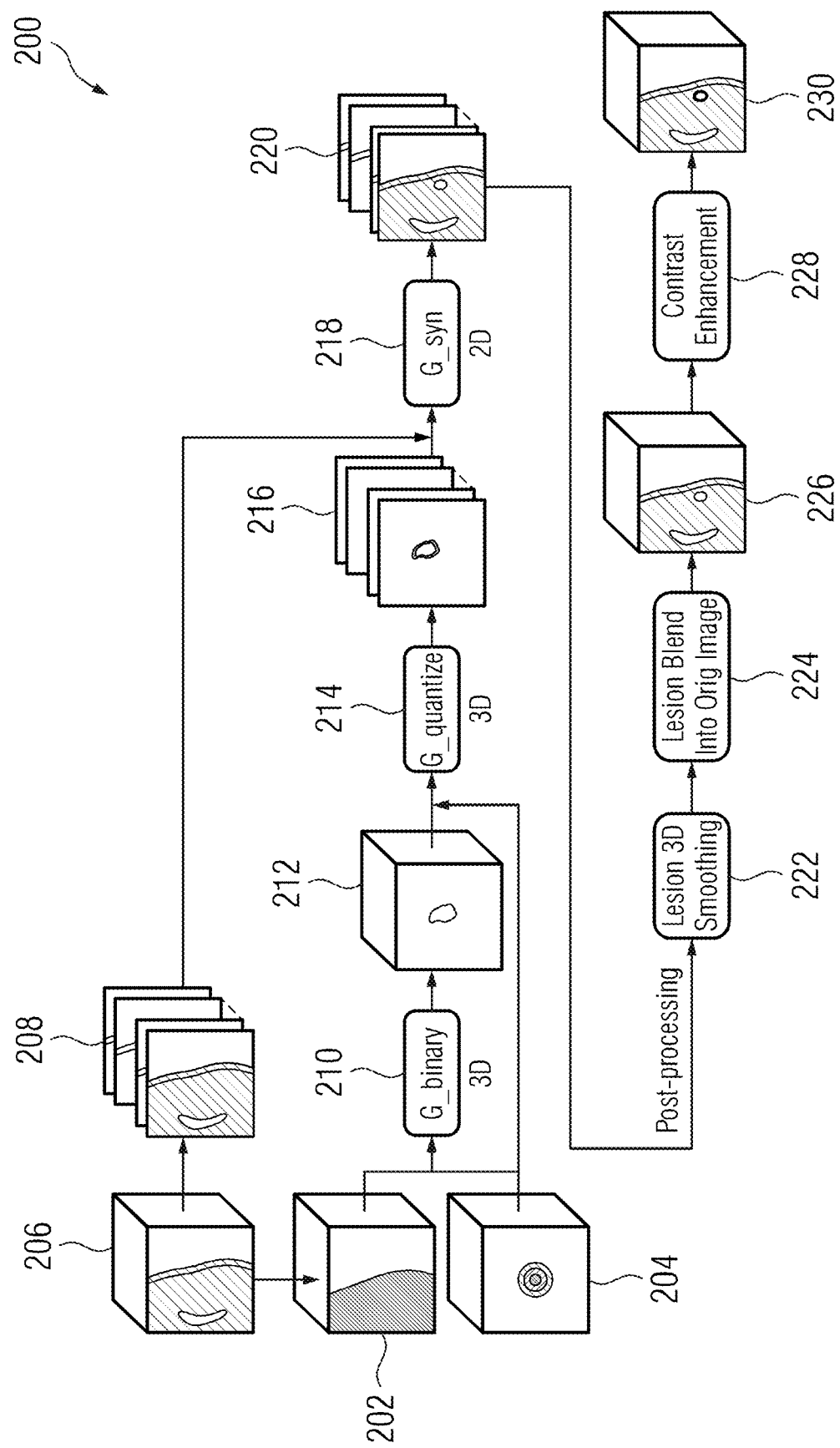
FIG. 2 shows a workflow for generating synthesized medical images of a tumor, in accordance with one or more embodiments.

FIG. 1 shows a method 100 for generating synthesized medical images of a tumor, in accordance with one or more embodiments. The steps of method 100 may be performed by one or more suitable computing devices, such as, e.g., computer 1102 of FIG. 11. FIG. 2 shows a workflow 200 for generating synthesized medical images of a tumor, in accordance with one or more embodiments. FIG. 1 and FIG. 2 will be described together.

At step 102 of FIG. 1, 1) a 3D mask of an anatomical structure generated from a 3D medical image and 2) a 3D image of a plurality of concentric spheres are received. In one example, as shown in workflow 200 of FIG. 2, the 3D mask of the anatomical structure is 3D mask 202 generated from 3D medical image 206 and the 3D image of the plurality of concentric spheres is 3D image 204.

3D mask 202 of the anatomical structure provides a voxel-wise identification of the anatomical structure in 3D medical image 206. For example, 3D mask 202 may be a 3D binary segmentation mask where, e.g., voxels having an intensity value of 1 correspond to the anatomical structure while voxels having an intensity value of 0 do not correspond to the anatomical structure. In one embodiment, the anatomical structure is a brain of a patient or a healthy subject (e.g., a person). However, the anatomical structure may be any other suitable organ, vessel, bone, etc. of the patient or healthy subject.

3D mask 202 of the anatomical structure may be generated from 3D medical image 206 using any suitable approach. In one example, 3D mask 202 of the anatomical structure is automatically generated from 3D medical image 206 using a machine learning based segmentation network. In another example, 3D mask 202 of the anatomical structure is manually generated from 3D medical image 206 by a user. 3D medical image 206 may be an MRI (medical resonance imaging) image, a CT (computed tomography) image, an ultrasound image, or a 3D medical image of any other suitable modality. In one embodiment, instead of receiving 3D mask 202 of the anatomical structure at step 102 of FIG. 1, 3D medical image 206 is received and 3D mask 202 of the anatomical structure is generated from 3D medical image 206.

3D image 204 of the plurality of concentric spheres encodes the properties of the tumor to be generated in the plurality of concentric spheres. For example, in one or more embodiments, the center of the concentric spheres defines the mass center location of the tumor, the size of the outermost sphere defines the overall size of the tumor, and the ratio of the sizes and intensity values of the concentric spheres defines the structure of the tumor. The location and/or size of the concentric spheres may be randomly selected or user defined. In one embodiment, 3D image 204 depicts three concentric spheres. In this embodiment, for example, the three concentric spheres may define an intensity value of 0.5 between the outermost sphere and the middle sphere, an intensity value of 0.75 between the middle sphere and the innermost sphere, and an intensity value of 1.0 within the innermost sphere. However, 3D image 204 may depict any other suitable number of concentric spheres greater than one and any other suitable intensity values.

3D mask 202 of the anatomical structure and/or 3D image 204 of the plurality of concentric spheres may be received by loading 3D mask 202 of the anatomical structure and/or 3D image 204 of the plurality of concentric spheres from a storage or memory of a computer system or receiving 3D mask 202 of the anatomical structure and/or 3D image 204 of the plurality of concentric spheres from a remote computer system.

At step 104 of FIG. 1, a 3D mask of a tumor is generated based on the 3D mask of the anatomical structure and the 3D image of the plurality of concentric spheres using a first 3D generator network. In one example, as shown in FIG. 2, 3D generator network $G_{binary}$ 210 receives as input 3D mask 202 of the anatomical structure and 3D image 204 of a plurality of concentric spheres and generates as output 3D mask 212 of the tumor.

3D mask 212 of the tumor provides a voxel-wise identification of the tumor to be generated to define size, shape, and location of the tumor. For example, 3D mask 212 of the tumor may be a 3D binary segmentation mask where, e.g., voxels having an intensity value of 1 correspond to the tumor while voxels having an intensity value of 0 do not correspond to the tumor. 3D generator network $G_{binary}$ 210 maps the size and location of the outermost sphere in 3D image 204, relative to the location of the anatomical structure identified in 3D mask 202, to the size, shape, and location of the tumor defined in 3D mask 212. The tumor may include a lesion, a hemorrhage, or any other anatomical abnormality.

At step 106 of FIG. 1, a 3D intensity map of the tumor is generated based on the 3D mask of the tumor and the 3D image of the plurality of concentric spheres using a second 3D generator network. In one example, as shown in FIG. 2, 3D generator network $G_{quantize}$ 214 receives as input 3D mask 212 of the tumor and 3D image 204 of a plurality of concentric spheres and generates as output 3D intensity map 216 of the tumor at several discrete gray levels. 3D intensity map 216 is formed on a plurality of 2D cross-section slices, as shown in FIG. 2.

3D generator network $G_{quantize}$ 214 maps the plurality of concentric spheres in 3D image 204, relative to the tumor defined in 3D mask 212 of the tumor, to quantized intensity values of pixels in 3D intensity map 216. The pixels of the tumor in 3D intensity map 216 have quantized intensity values, e.g., ranging between 0 and 1, to capture the coarse 3D structure of the tumor.

At step 108 of FIG. 1, a 3D synthesized medical image of the tumor is generated based on one or more 2D slices of the 3D intensity map of the tumor and one or more 2D slices of the 3D medical image using a 2D generator network. In one example, as shown in FIG. 2, 2D generator network $G_{syn}$ 218 receives as input one or more 2D slices extracted from 3D intensity map 216 and one or more 2D slices 208 extracted from 3D medical image 206 and generates as output 2D synthesized medical images 220 of the tumor. 2D generator network $G_{syn}$ 218 maps the intensity values of pixels in 2D slices of 3D intensity map 216 to the structure of the tumor to generate 2D synthesized medical images 220 of the tumor. Each 2D synthesized medical images 220 thus depicts a recreation of a respective slice 208 with a cross-sectional view of the synthesized tumor overlaid thereon. 2D synthesized medical images 220 represent cross-sectional 2D slices that together form a 3D synthesized medical image of the tumor. Thus, once all the 2D synthesized medical images 220 for the 3D volume are synthesized, they are stacked into the 3D synthesized medical image of the tumor.

At step 110 of FIG. 1, in some optional embodiments, the 3D synthesized medical images are post-processed. In one example, as shown in workflow FIG. 2, lesion 3D smoothing 222 is applied to smooth the synthesized tumor in the 3D synthesized medical image (formed by 2D synthesized medical images 220) using a 3D Gaussian kernel. Lesion blending 224 is then performed by extracting the smoothed synthesized tumors from the smoothed 3D synthesized medical image and blending the extracted smoothed synthesized tumors into the original 3D medical image 206 using 3D mask 212 to generate a 3D blended synthesized medical image. Optionally, contrast enhancement 228 is performed to adjust (e.g., enhance or reduce) the contrast of the tumor in 3D blended synthesized medical image 226 as needed to generate the final 3D synthesized medical image 230 of the tumor. The contrast adjustment may be random or user-defined.

At step 112 of FIG. 1, the 3D synthesized medical image of the tumor is output. For example, the 3D synthesized medical image of the tumor (e.g., generated at step 108 and/or 110) can be output by displaying the 3D synthesized medical image of the tumor on a display device of a computer system, storing the 3D synthesized medical image of the tumor on a memory or storage of a computer system, or by transmitting the 3D synthesized medical image of the tumor to a remote computer system. In one embodiment, the 3D synthesized medical image of the tumor is stored as part of an augmented training dataset and used for training a machine learning based network for performing a medical imaging analysis task, such as, e.g., detection, segmentation, classification, etc. of a tumor.

Advantageously, 3D generator network $G_{binary}$ 210 for generating 3D mask 212 of the tumor and 3D generator network $G_{quantize}$ 214 for generating 3D intensity map 216 are implemented using 3D neural networks, enabling the synthesized tumor generated in the 3D synthesized medical image (formed by stacking 2D synthesized medical images 220) to have continuous structure in all three dimensions, while 2D generator network $G_{syn}$ 218 for generating 2D synthesized medical images 220 is trained with a 2D perceptual loss so that the visual perception of synthesized tumor is realistic.

Figure 3:
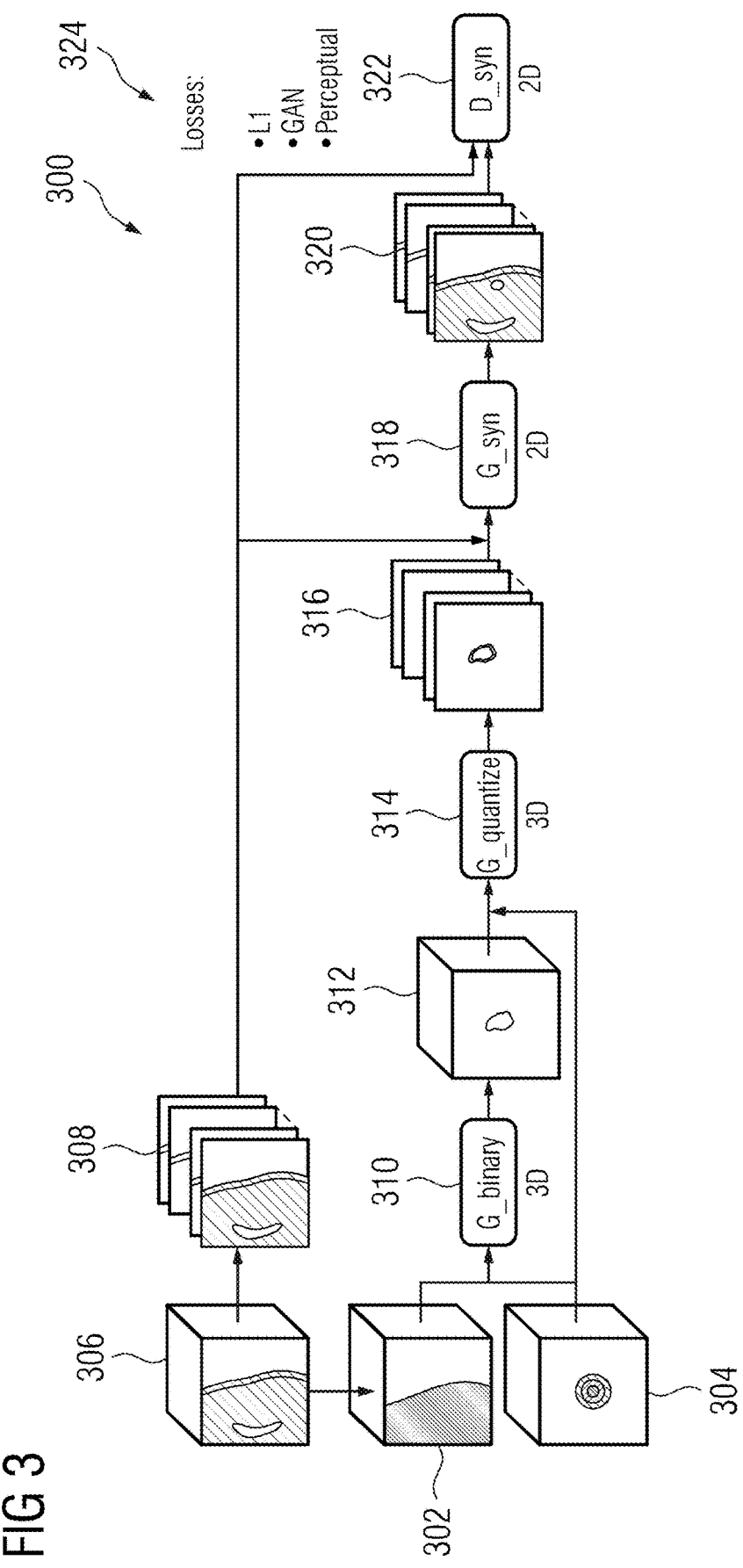
FIG. 3 shows a workflow for training 3D-2D networks for generating synthesized medical images of a tumor, in accordance with one or more embodiments.

FIG. 3 shows a workflow 300 for training 3D-2D networks for generating synthesized medical images of a tumor, in accordance with one or more embodiments. Workflow 300 of FIG. 3 is performed during a prior offline or training stage. Once trained, the trained networks are utilized during an online or inference stage (e.g., to perform one or more steps of method 100 of FIG. 1 or one or more operations of workflow 200 of FIG. 2) for generating synthesized medical images of a tumor.

Workflow 300 comprises 3D generator network $G_{binary}$ 310, 3D generator network $G_{quantize}$ 314, and 2D generator network $G_{syn}$ 318. In some examples, 3D generator network $G_{binary}$ 310 may be the first 3D generator network utilized at step 104 of FIG. 1 or 3D generator network $G_{binary}$ 210 of FIG. 2, 3D generator network $G_{quantize}$ 314 may be the second 3D generator network utilized at step 106 of FIG. 1 or 3D generator network $G_{quantize}$ 214 of FIGS. 2, and 2D generator network $G_{syn}$ 318 may be the 2D generator network utilized at step 108 of FIG. 1 or 2D generator network $G_{syn}$ 218 of FIG. 2.

3D generator network $G_{binary}$ 310, 3D generator network $G_{quantize}$ 314, and 2D generator network $G_{syn}$ 318 may be implemented using any suitable machine learning based network. In one embodiment, 3D generator network $G_{binary}$ 310 and 3D generator network $G_{quantize}$ 314 are implemented using 3D UNet or UNet-like networks or 3D encoder-decoder networks and 2D generator network $G_{syn}$ 318 is implemented using a 2D encoder-decoder network.

As shown in workflow 300, 3D generator network $G_{binary}$ 310 is trained using 1) 3D training mask 302 of an anatomical structure generated from 3D training medical image 306, 2) 3D training image 304 of a plurality of concentric spheres, and 3) 3D training mask 312 of a tumor. 3D generator network $G_{quantize}$ 314 is trained using 1) 3D training mask 312 of a tumor, 2) 3D training image 304 of a plurality of concentric spheres, and 3) 3D training intensity maps 316 of the tumor. 2D generator network $G_{syn}$ 318 is trained using 1) 2D training intensity maps 316 of the tumor, 2) 2D training slices 308 extracted from 3D training medical image 306, and 3) 2D synthesized medical images 220 of the tumor. In one embodiment, 3D training image 304 of a plurality of concentric spheres and 3D training intensity maps 316 are generated according to workflow 400 of FIG. 4, described in further detail below. 2D training intensity maps 316 are generated by unstacking the 3D training intensity maps 316 into 2D slices.

3D generator network $G_{binary}$ 310, 3D generator network $G_{quantize}$ 314, and 2D generator network $G_{syn}$ 318 are trained according to one or more loss functions 324. In one embodiment, 3D generator network $G_{binary}$ 310 and 3D generator network $G_{quantize}$ 314 are trained with a 3D L1 loss, while 2D generator network $G_{syn}$ 318 is trained with a 2D L1 loss, a GAN loss, and a 2D perceptual loss. The 2D L1 loss, the GAN loss, and the 2D perceptual loss may be applied to 2D training synthesized medical images 320 of the tumor along one axis or along all three perpendicular axes for training 2D generator network $G_{syn}$ 318.

2D generator network $G_{syn}$ 318 is trained with adversarial loss using 2D discriminator network $D_{syn}$ 322. 2D discriminator network $D_{syn}$ 322 attempts to distinguish between 2D training synthesized medical images 320 and 2D training slices 308. Accordingly, 2D discriminator network $D_{syn}$ 322 guides 2D generator network $G_{syn}$ 318 to generate realistic 2D training synthesized medical images 320 that are indistinguishable from the real 2D training slices 308. 2D discriminator network $D_{syn}$ 322 is only utilized during the training stage and is not utilized during the inference stage.

Figure 4:
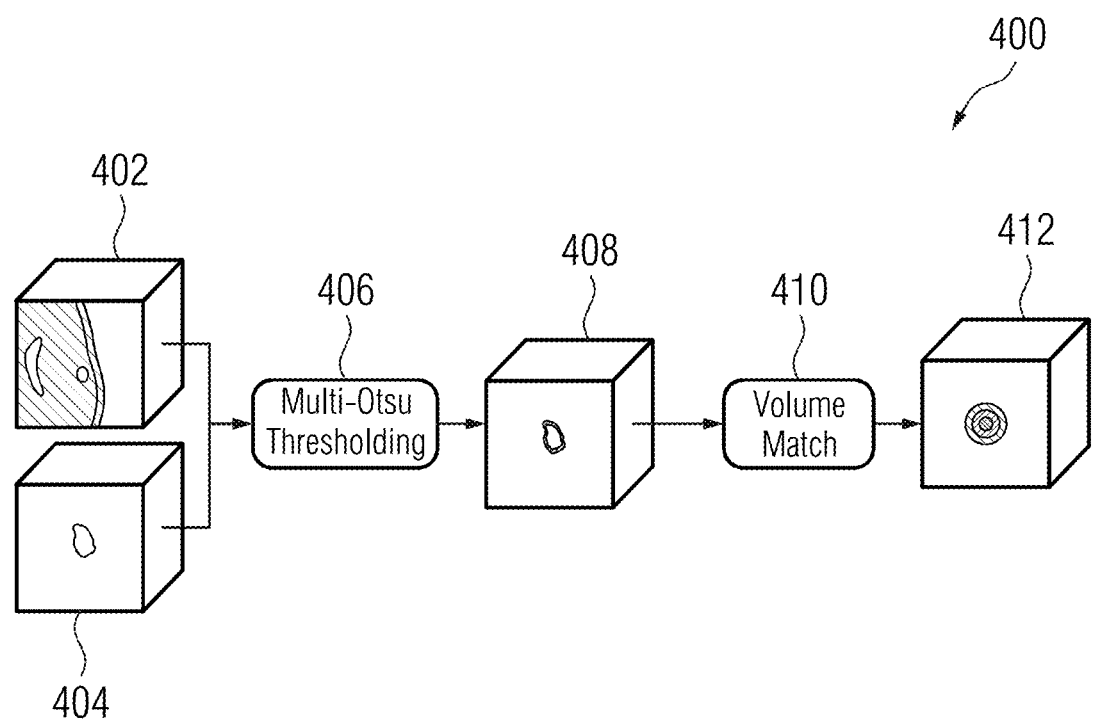
FIG. 4 shows a workflow for generating 3D training images of a plurality of concentric spheres and 3D training intensity maps of the tumor, in accordance with one or more embodiments.

FIG. 4 shows a workflow 400 for generating 3D training images of a plurality of concentric spheres and 3D training intensity maps, in accordance with one or more embodiments. The 3D training images of a plurality of concentric spheres and 3D training intensity maps may be utilized in workflow 300 of FIG. 3 for training 3D-2D networks for generating synthesized medical images of a tumor.

Workflow 400 starts with 3D training medical image 402 depicting a tumor and 3D training mask 404 representing the ground truth segmentation of the tumor in 3D training medical image 402. Multi-Otsu thresholding 406 is applied to 3D training medical image 402 and 3D training mask 404 to generate a 3D training intensity map 408. Multi-Otsu thresholding 406 separates voxels of 3D training medical image 402 within the tumor identified in 3D training mask 404 into one of a plurality of classes. Multi-Otsu thresholding 406 automatically calculates one or more thresholds to classify the voxels. In one embodiment, where the goal is to generate 3D training images of three concentric spheres, multi-Otsu thresholding 406 calculates two thresholds. FIG. 4 shows 3D training intensity map 408 with voxels of the tumor classified to one of three classes. Volume match 410 is then performed on 3D training intensity map 408 to generate 3D training image 412 of three concentric spheres. To perform volume match 410, each of the concentric spheres is associated with a respective category and the volume of voxels in each category in 3D training intensity map 408 is the volume of the associated sphere in 3D training image 412. The center of the concentric spheres in 3D training image 412 is defined as the mass center of the tumor in 3D training intensity map 408.

Embodiments described herein were experimentally validated to synthesize brain MR images of brain metastases. The validation dataset comprised T1-weighted 3D MP-RAGE (magnetization-prepared rapid gradient-echo) post-contrast brain MR images of 800 human subjects with a total of 2688 metastasis lesions. The clinically treated metastases were annotated by radiation oncologists, while the untreated metastases were annotated by radiologists. For data preprocessing, all images were resized to 256×256×original number of axial slices. Each 3D MR volume's minimum voxel intensity to the 98$^{th}$ percentile range was normalized to [0,1]. Brain masks were generated using a deep learning model. For each metastasis lesion, 3D cubes of size 64×64×64 centered at the lesion were extracted from the original image, the corresponding segmentation mask, and the brain mask. To reflect the original spatial relationship, each brain mask was multiplied with a 3D Gaussian probability density function before being extracted to the smaller 3D cube.

During the experiments, to investigate the contribution of synthetic data augmentation at different data scales, the network was trained with 10%, 30%, 50%, and 100% of the synthetic data. Within each training data scale, two network up-sampling strategies for generating the quantized intensity map were evaluated: "transposed convolution" and "up-sampling+convolution." During inference, a set of concentric spheres from the dataset were randomly sampled and used as the starting point to generate brain metastasis lesions onto another set of randomly sampled brain MR images. A radiologist reviewed 1500 synthetic images in each combination of the training data scale and network architecture to evaluate the synthetic metastasis images. A synthetic metastasis image was deemed indistinguishable if the radiologist could not tell whether it was a synthetic lesion or real lesion.

Figure 5:
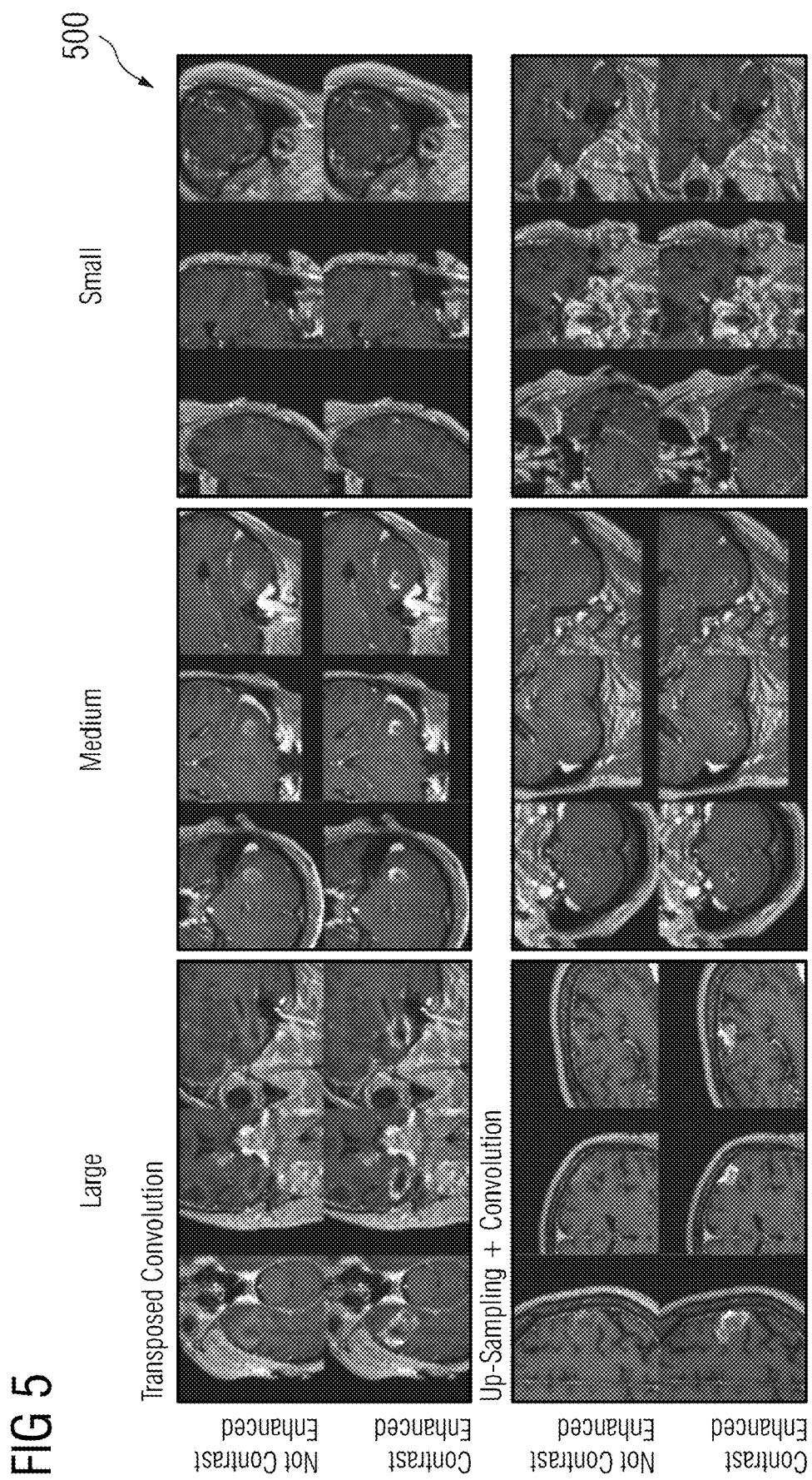
FIG. 5 shows synthesized medical images of lesions generated in accordance with embodiments described herein.

FIG. 5 shows synthesized medical images 500 of lesions generated in accordance with embodiments described herein. The lesions in synthesized medical images 500 are generated with different locations, sizes, structures, up-sampling strategies, and with and without contrast enhancement. Each synthesized lesion is at the center of each image in axial, coronal, and sagittal views. As shown in FIG. 5, images 500 confirm the spatial continuity and realistic appearance in different configurations and demonstrates the effectiveness of the configurable parameters according to embodiments described herein.

Figure 6:
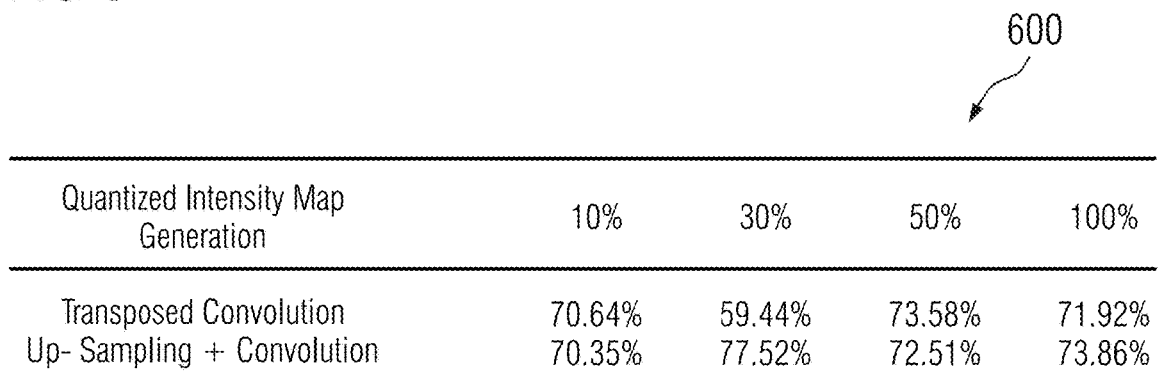
FIG. 6 shows a table showing the indistinguishability rate of synthesized medical images generated in accordance with one or more embodiments described herein.

FIG. 6 shows a table 600 showing the indistinguishability rate of synthesized medical images generated in accordance with one or more embodiments described herein. The indistinguishability rate was determined as the proportion of synthetic medical images that could not be distinguished from real brain metastasis images in a review by a radiologist. As can be seen in table 600, all indistinguishability rates after contrast enhancement are above 70%. Only the result from the training with 30% data without contrast enhancement is below 70%. The main reason for this is due to not enough contrast in the synthesized lesion area, which can be compensated with the contrast enhancement during postprocessing, in accordance with embodiments described herein. For all other groups, the failed cases are mainly due to elongated lesion shape in one direction for very large lesions, no surrounding mass effect for very large lesions, or boundary-crossing lesion location.

Figure 7:
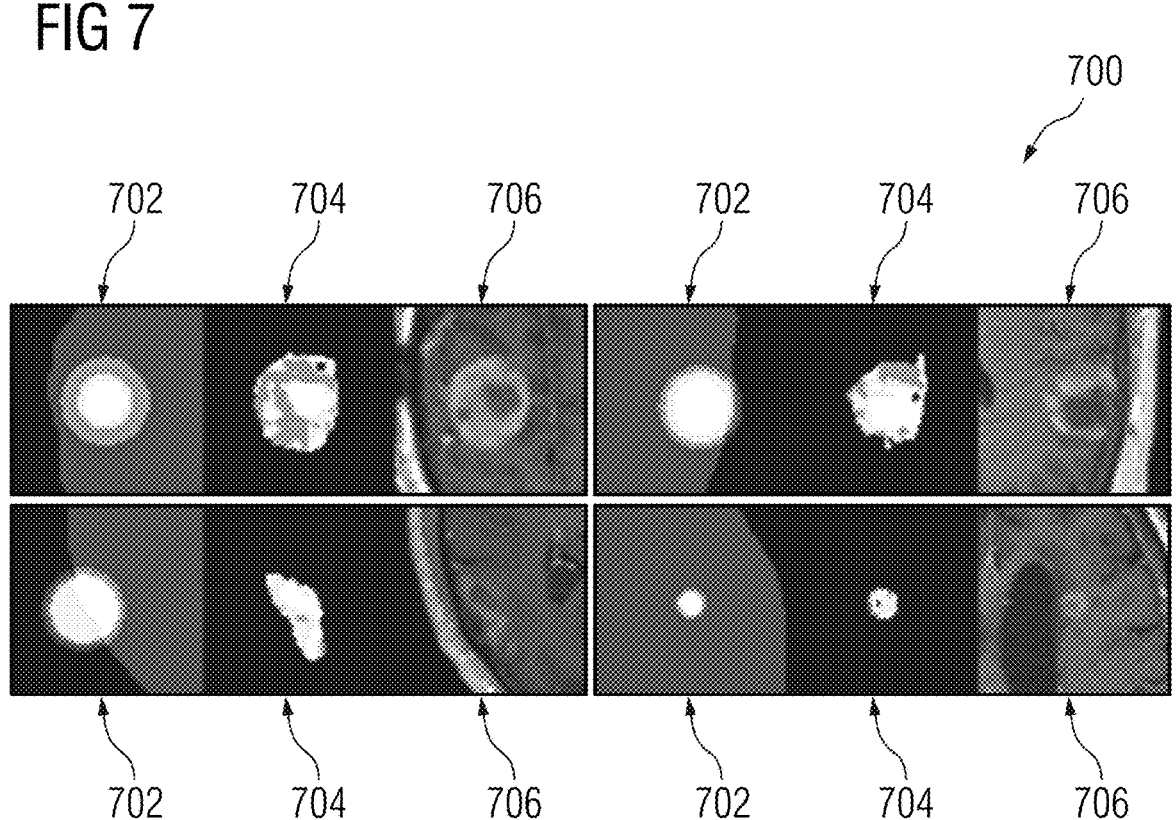
FIG. 7 shows exemplary images generated in accordance with embodiments described herein.

FIG. 7 shows exemplary images 700 generated in accordance with embodiments described herein. Images 700 comprise synthesized medical images 706 of a tumor, which are generated from images 702 of three concentric spheres with different locations, sizes, and volume ratios, via images 704 of corresponding intermediate quantized intensity maps. Images 700 demonstrate the effectiveness of the configurable parameters to control the location, size, and structure of the brain metastases.

Figure 8:
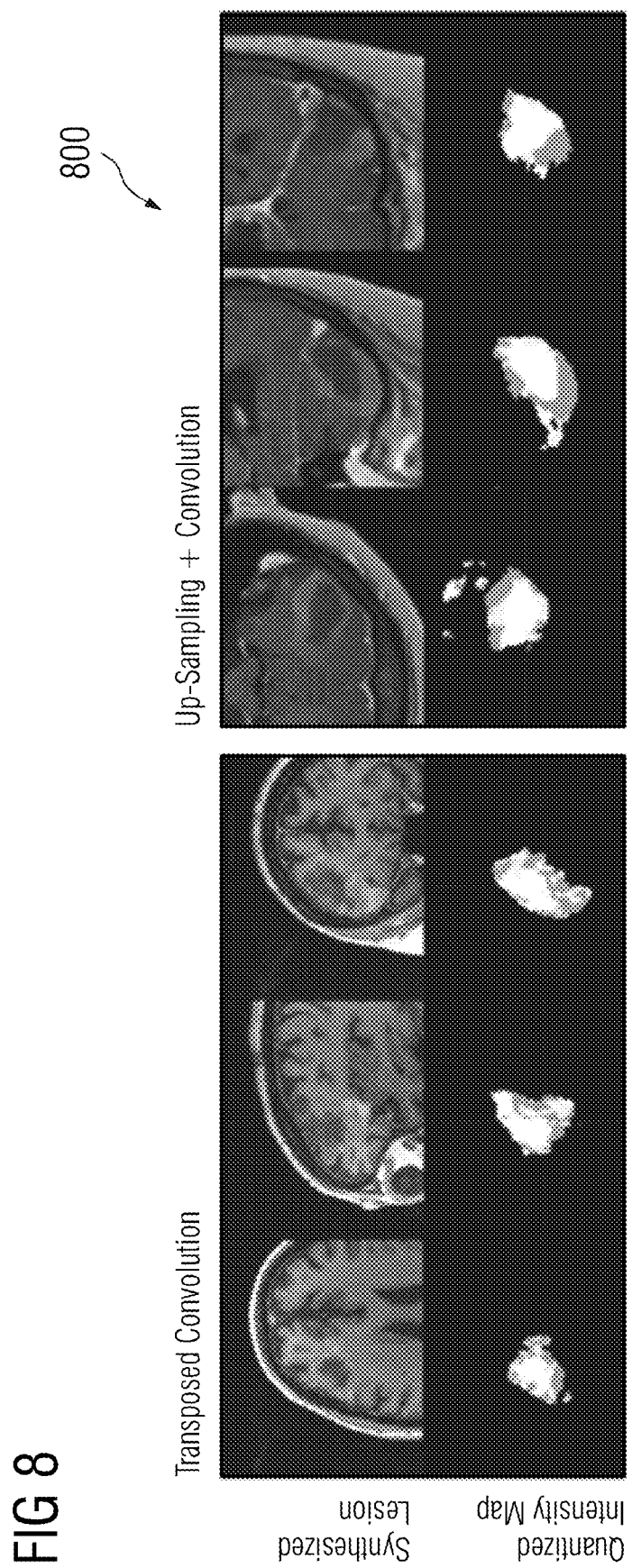
FIG. 8 shows images comparing synthesized lesions generated by the "transposed convolution" and the "upsampling+convolution up-sampling" strategies with the corresponding intermediate quantized intensity maps, in accordance with embodiments described herein.

FIG. 8 shows images 800 comparing synthesized lesions generated by the "transposed convolution" and the "up-sampling+convolution up-sampling" strategies with the corresponding intermediate quantized intensity maps, in accordance with embodiments described herein. As shown in FIG. 5, the structure of the quantized intensity maps and the corresponding synthesized lesion by transposed convolution is more heterogeneous. This is due to the shape-smooth characteristics of the up-sampling+convolution strategy. In this way, the lesions are synthesized with smooth or heterogeneous appearance as needed, which helps to improve the diversity in the overall data augmentation. It can further be seen from FIG. 8 that with the structure-wise guidance from the 3D quantized intensity map, the synthesized lesions appear continuous in all three dimensions, and due to the 2D perceptual loss the synthesized lesion maintains a realistic appearance.

Embodiments described herein are described with respect to the claimed systems as well as with respect to the claimed methods. Features, advantages or alternative embodiments herein can be assigned to the other claimed objects and vice versa. In other words, claims for the systems can be improved with features described or claimed in the context of the methods. In this case, the functional features of the method are embodied by objective units of the providing system.

Furthermore, certain embodiments described herein are described with respect to methods and systems utilizing trained machine learning based networks (or models), as well as with respect to methods and systems for training machine learning based networks. Features, advantages or alternative embodiments herein can be assigned to the other claimed objects and vice versa. In other words, claims for methods and systems for training a machine learning based network can be improved with features described or claimed in context of the methods and systems for utilizing a trained machine learning based network, and vice versa.

In particular, the trained machine learning based networks applied in embodiments described herein can be adapted by the methods and systems for training the machine learning based networks. Furthermore, the input data of the trained machine learning based network can comprise advantageous features and embodiments of the training input data, and vice versa. Furthermore, the output data of the trained machine learning based network can comprise advantageous features and embodiments of the output training data, and vice versa.

In general, a trained machine learning based network mimics cognitive functions that humans associate with other human minds. In particular, by training based on training data, the trained machine learning based network is able to adapt to new circumstances and to detect and extrapolate patterns.

In general, parameters of a machine learning based network can be adapted by means of training. In particular, supervised training, semi-supervised training, unsupervised training, reinforcement learning and/or active learning can be used. Furthermore, representation learning (an alternative term is "feature learning") can be used. In particular, the parameters of the trained machine learning based network can be adapted iteratively by several steps of training.

In particular, a trained machine learning based network can comprise a neural network, a support vector machine, a decision tree, and/or a Bayesian network, and/or the trained machine learning based network can be based on k-means clustering, Q-learning, genetic algorithms, and/or association rules. In particular, a neural network can be a deep neural network, a convolutional neural network, or a convolutional deep neural network. Furthermore, a neural network can be an adversarial network, a deep adversarial network and/or a generative adversarial network.

Figure 9:
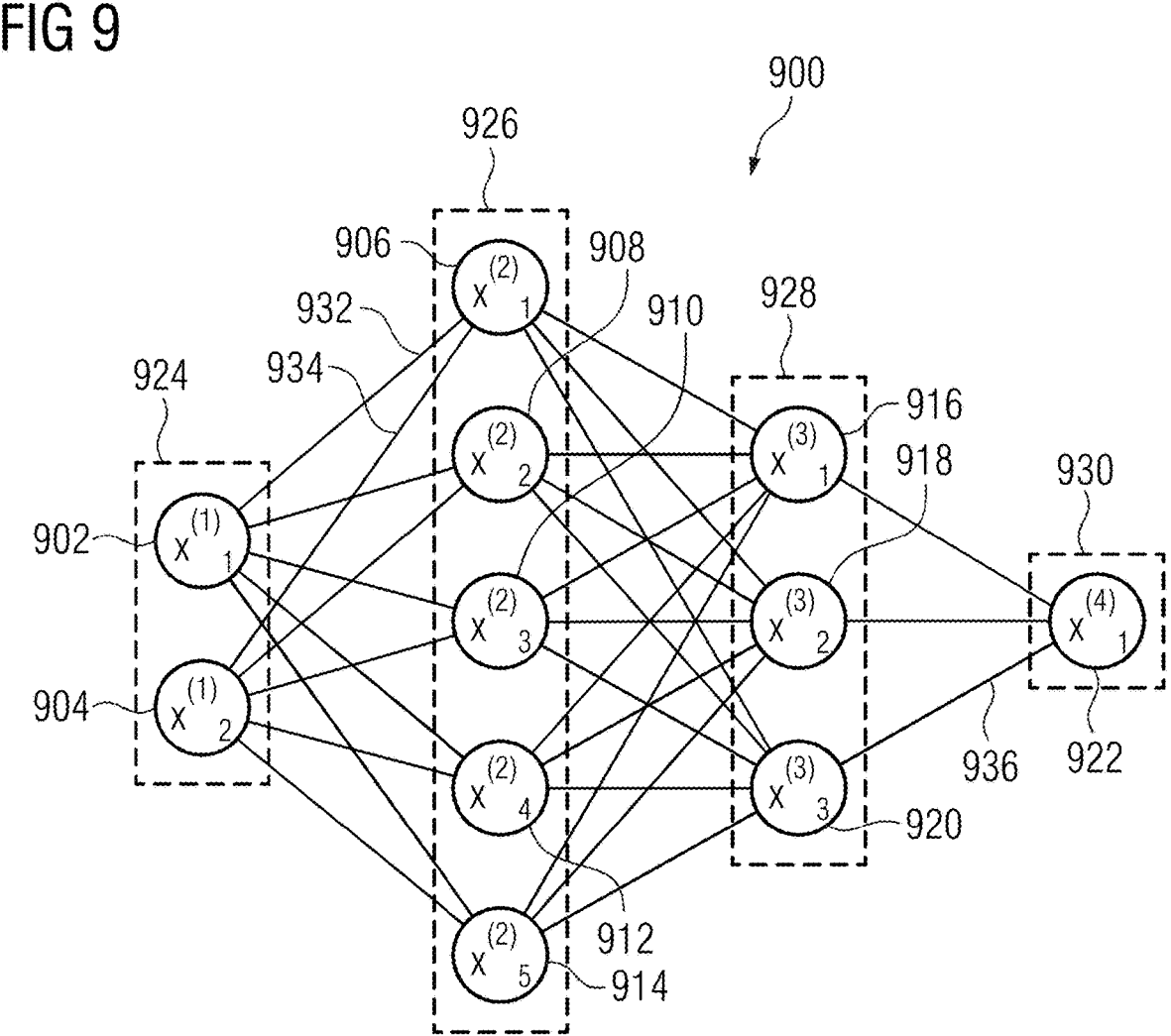
FIG. 9 shows an exemplary artificial neural network that may be used to implement one or more embodiments.

FIG. 9 shows an embodiment of an artificial neural network 900, in accordance with one or more embodiments. Alternative terms for "artificial neural network" are "neural network", "artificial neural net" or "neural net". Machine learning networks described herein, such as, e.g., first 3D generator network utilized at step 104, the second 3D generator network utilized at step 106, and the 2D generator network utilized at step 108 of FIG. 1; 3D generator network $G_{binary}$ 210, 3D generator network $G_{quantize}$ 214, 2D generator network $G_{syn}$ 218 of FIG. 2; and 3D generator network $G_{binary}$ 310, 3D generator network $G_{quantize}$ 314, 2D generator network $G_{syn}$ 318, and 2D discriminator network $D_{syn}$ 322 of FIG. 3, may be implemented using artificial neural network 900.

The artificial neural network 900 comprises nodes 902-922 and edges 932, 934, ..., 936, wherein each edge 932, 934, ..., 936 is a directed connection from a first node 902-922 to a second node 902-922. In general, the first node 902-922 and the second node 902-922 are different nodes 902-922, it is also possible that the first node 902-922 and the second node 902-922 are identical. For example, in FIG. 9, the edge 932 is a directed connection from the node 902 to the node 906, and the edge 934 is a directed connection from the node 904 to the node 906. An edge 932, 934, ..., 936 from a first node 902-922 to a second node 902-922 is also denoted as "ingoing edge" for the second node 902-922 and as "outgoing edge" for the first node 902-922.

In this embodiment, the nodes 902-922 of the artificial neural network 900 can be arranged in layers 924-930, wherein the layers can comprise an intrinsic order introduced by the edges 932, 934, ..., 936 between the nodes 902-922. In particular, edges 932, 934, ..., 936 can exist only between neighboring layers of nodes. In the embodiment shown in FIG. 9, there is an input layer 924 comprising only nodes 902 and 904 without an incoming edge, an output layer 930 comprising only node 922 without outgoing edges, and hidden layers 926, 928 in-between the input layer 924 and the output layer 930. In general, the number of hidden layers 926, 928 can be chosen arbitrarily. The number of nodes 902 and 904 within the input layer 924 usually relates to the number of input values of the neural network 900, and the number of nodes 922 within the output layer 930 usually relates to the number of output values of the neural network 900.

In particular, a (real) number can be assigned as a value to every node 902-922 of the neural network 900. Here, $x^{(n)}_i$ denotes the value of the i-th node 902-922 of the n-th layer 924-930. The values of the nodes 902-922 of the input layer 924 are equivalent to the input values of the neural network 900, the value of the node 922 of the output layer 930 is equivalent to the output value of the neural network 900. Furthermore, each edge 932, 934, ..., 936 can comprise a weight being a real number, in particular, the weight is a real number within the interval $[-1, 1]$ or within the interval $[0, 1]$. Here, $w^{(m,n)}_{i,j}$ denotes the weight of the edge between the i-th node 902-922 of the m-th layer 924-930 and the j-th node 902-922 of the n-th layer 924-930. Furthermore, the abbreviation $w^{(n)}_{i,j}$ is defined for the weight $w^{(n,n+1)}_{i,j}$.

In particular, to calculate the output values of the neural network 900, the input values are propagated through the neural network. In particular, the values of the nodes 902-922 of the (n+1)-th layer 924-930 can be calculated based on the values of the nodes 902-922 of the n-th layer 924-930 by $$x_j^{(n+1)} = f(\Sigma_i x_i^{(n)} \cdot w_{i,j}^{(n)}).$$

Herein, the function f is a transfer function (another term is "activation function"). Known transfer functions are step functions, sigmoid function (e.g. the logistic function, the generalized logistic function, the hyperbolic tangent, the Arctangent function, the error function, the smoothstep function) or rectifier functions. The transfer function is mainly used for normalization purposes.

In particular, the values are propagated layer-wise through the neural network, wherein values of the input layer 924 are given by the input of the neural network 900, wherein values of the first hidden layer 926 can be calculated based on the values of the input layer 924 of the neural network, wherein values of the second hidden layer 928 can be calculated based in the values of the first hidden layer 926, etc.

In order to set the values $w^{(m,n)}_{i,j}$ for the edges, the neural network 900 has to be trained using training data. In particular, training data comprises training input data and training output data (denoted as $t_i$). For a training step, the neural network 900 is applied to the training input data to generate calculated output data. In particular, the training data and the calculated output data comprise a number of values, said number being equal with the number of nodes of the output layer.

In particular, a comparison between the calculated output data and the training data is used to recursively adapt the weights within the neural network 900 (backpropagation algorithm). In particular, the weights are changed according to $$w_{i,j}^{(n)\prime} = w_{i,j}^{(n)} - \gamma \cdot \delta_j^{(n)} \cdot x_i^{(n)}$$

wherein $\gamma$ is a learning rate, and the numbers $\delta^{(n)}_j$ can be recursively calculated as $$\delta_j^{(n)} = (x_k^{(n+1)} - t_j^{(n+1)}) \cdot f'(\Sigma_i x_i^{(n)} \cdot w_{i,j}^{(n)})$$

based on $\delta^{(n+1)}_j$, if the $(n+1)$-th layer is not the output layer, and $$\delta_j^{(n)} = (x_k^{(n+1)} - t_j^{(n+1)}) \cdot f'(\Sigma_i x_i^{(n)} \cdot w_{i,j}^{(n)})$$

if the $(n+1)$-th layer is the output layer 930, wherein f' is the first derivative of the activation function, and $y^{(n+1)}_j$ is the comparison training value for the j-th node of the output layer 930.

Figure 10:
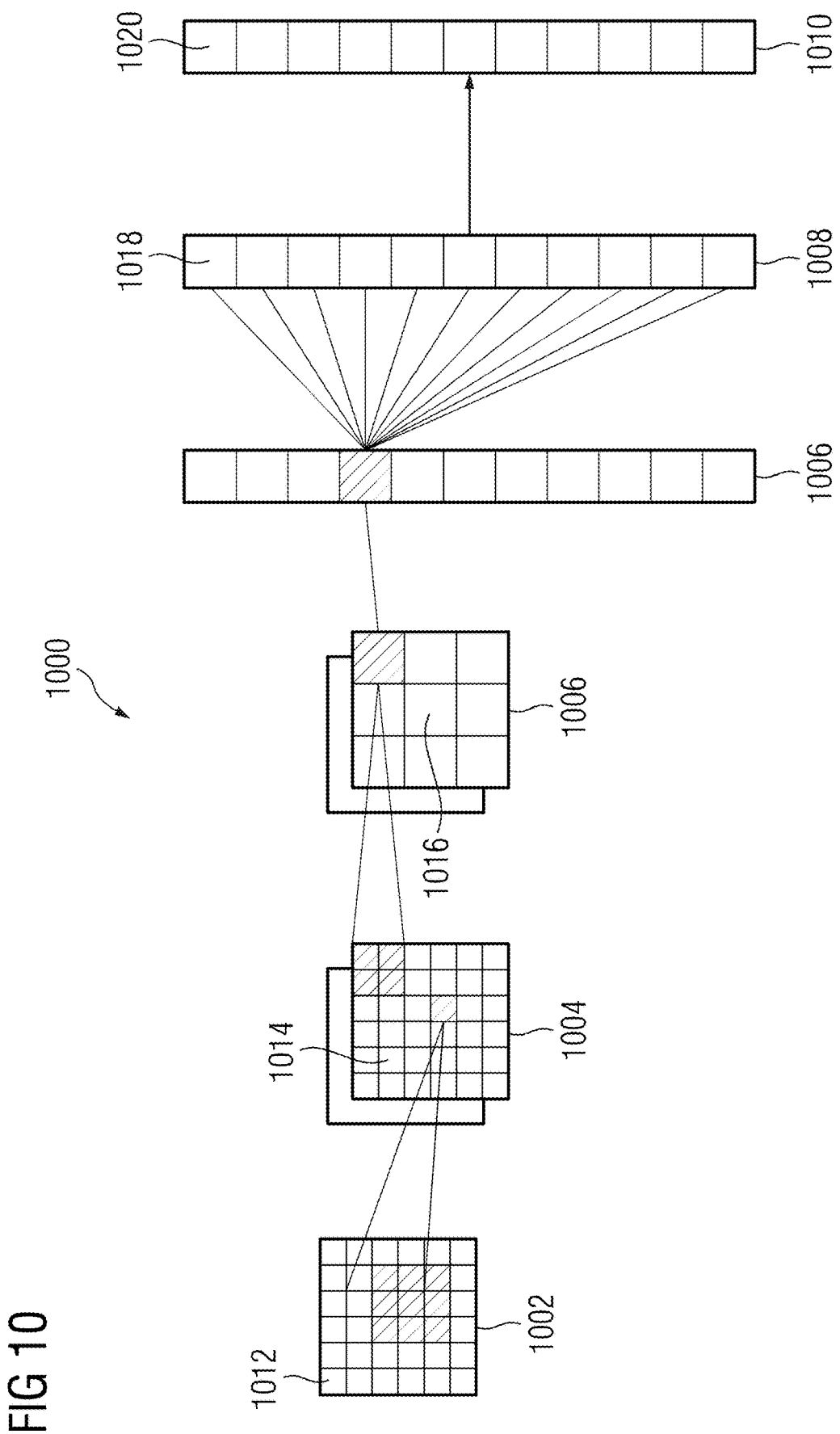
FIG. 10 shows a convolutional neural network that may be used to implement one or more embodiments.

FIG. 10 shows a convolutional neural network 1000, in accordance with one or more embodiments. Machine learning networks described herein, such as, e.g., first 3D generator network utilized at step 104, the second 3D generator network utilized at step 106, and the 2D generator network utilized at step 108 of FIG. 1; 3D generator network $G_{binary}$ 210, 3D generator network $G_{quantize}$ 214, 2D generator network $G_{syn}$ 218 of FIG. 2; and 3D generator network $G_{binary}$ 310, 3D generator network $G_{quantize}$ 314, 2D generator network $G_{syn}$ 318, and 2D discriminator network $D_{syn}$ 322 of FIG. 3, may be implemented using convolutional neural network 1000.

In the embodiment shown in FIG. 10, the convolutional neural network comprises 1000 an input layer 1002, a convolutional layer 1004, a pooling layer 1006, a fully connected layer 1008, and an output layer 1010. Alternatively, the convolutional neural network 1000 can comprise several convolutional layers 1004, several pooling layers 1006, and several fully connected layers 1008, as well as other types of layers. The order of the layers can be chosen arbitrarily, usually fully connected layers 1008 are used as the last layers before the output layer 1010.

In particular, within a convolutional neural network 1000, the nodes 1012-1020 of one layer 1002-1010 can be considered to be arranged as a d-dimensional matrix or as a d-dimensional image. In particular, in the two-dimensional case the value of the node 1012-1020 indexed with i and j in the n-th layer 1002-1010 can be denoted as $x^{(n)}_{[i,j]}$. However, the arrangement of the nodes 1012-1020 of one layer 1002-1010 does not have an effect on the calculations executed within the convolutional neural network 1000 as such, since these are given solely by the structure and the weights of the edges.

In particular, a convolutional layer 1004 is characterized by the structure and the weights of the incoming edges forming a convolution operation based on a certain number of kernels. In particular, the structure and the weights of the incoming edges are chosen such that the values $x^{(n)}_k$ of the nodes 1014 of the convolutional layer 1004 are calculated as a convolution $x^{(n)}_k = K_k * x^{(n-1)}$ based on the values $x^{(n-1)}$ of the nodes 1012 of the preceding layer 1002, where the convolution * is defined in the two-dimensional case as $$x_k^{(n)}[i,j] = (K_k * x^{(n-1)})[i,j] = \Sigma_{i'} \Sigma_{j'} K_k[i',j'] \cdot x^{(n-1)}[i-i',j-j'].$$

Here the k-th kernel $K_k$ is a d-dimensional matrix (in this embodiment a two-dimensional matrix), which is usually small compared to the number of nodes 1012-1018 (e.g. a 3×3 matrix, or a 5×5 matrix). In particular, this implies that the weights of the incoming edges are not independent, but chosen such that they produce said convolution equation. In particular, for a kernel being a 3×3 matrix, there are only 9 independent weights (each entry of the kernel matrix corresponding to one independent weight), irrespectively of the number of nodes 1012-1020 in the respective layer 1002-1010. In particular, for a convolutional layer 1004, the number of nodes 1014 in the convolutional layer is equivalent to the number of nodes 1012 in the preceding layer 1002 multiplied with the number of kernels.

If the nodes 1012 of the preceding layer 1002 are arranged as a d-dimensional matrix, using a plurality of kernels can be interpreted as adding a further dimension (denoted as "depth" dimension), so that the nodes 1014 of the convolutional layer 1004 are arranged as a (d+1)-dimensional matrix. If the nodes 1012 of the preceding layer 1002 are already arranged as a (d+1)-dimensional matrix comprising a depth dimension, using a plurality of kernels can be interpreted as expanding along the depth dimension, so that the nodes 1014 of the convolutional layer 1004 are arranged also as a (d+1)-dimensional matrix, wherein the size of the (d+1)-dimensional matrix with respect to the depth dimension is by a factor of the number of kernels larger than in the preceding layer 1002.

The advantage of using convolutional layers 1004 is that spatially local correlation of the input data can exploited by enforcing a local connectivity pattern between nodes of adjacent layers, in particular by each node being connected to only a small region of the nodes of the preceding layer.

In embodiment shown in FIG. 10, the input layer 1002 comprises 36 nodes 1012, arranged as a two-dimensional 6×6 matrix. The convolutional layer 1004 comprises 72 nodes 1014, arranged as two two-dimensional 6×6 matrices, each of the two matrices being the result of a convolution of the values of the input layer with a kernel. Equivalently, the nodes 1014 of the convolutional layer 1004 can be interpreted as arranges as a three-dimensional 6×6×2 matrix, wherein the last dimension is the depth dimension.

A pooling layer 1006 can be characterized by the structure and the weights of the incoming edges and the activation function of its nodes 1016 forming a pooling operation based on a non-linear pooling function f. For example, in the two dimensional case the values $x^{(n)}$ of the nodes 1016 of the pooling layer 1006 can be calculated based on the values $x^{(n-1)}$ of the nodes 1014 of the preceding layer 1004 as $$x^{(n)}[i,j] = f(x^{(n-1)}[id_1, jd_2], \ldots, x^{(n-1)}[id_1 + d_1 - 1, jd_2 + d_2 - 1])$$

In other words, by using a pooling layer 1006, the number of nodes 1014, 1016 can be reduced, by replacing a number d1·d2 of neighboring nodes 1014 in the preceding layer 1004 with a single node 1016 being calculated as a function of the values of said number of neighboring nodes in the pooling layer. In particular, the pooling function f can be the max-function, the average or the L2-Norm. In particular, for a pooling layer 1006 the weights of the incoming edges are fixed and are not modified by training.

The advantage of using a pooling layer 1006 is that the number of nodes 1014, 1016 and the number of parameters is reduced. This leads to the amount of computation in the network being reduced and to a control of overfitting.

In the embodiment shown in FIG. 10, the pooling layer 1006 is a max-pooling, replacing four neighboring nodes with only one node, the value being the maximum of the values of the four neighboring nodes. The max-pooling is applied to each d-dimensional matrix of the previous layer; in this embodiment, the max-pooling is applied to each of the two two-dimensional matrices, reducing the number of nodes from 72 to 18.

A fully-connected layer 1008 can be characterized by the fact that a majority, in particular, all edges between nodes 1016 of the previous layer 1006 and the nodes 1018 of the fully-connected layer 1008 are present, and wherein the weight of each of the edges can be adjusted individually.

In this embodiment, the nodes 1016 of the preceding layer 1006 of the fully-connected layer 1008 are displayed both as two-dimensional matrices, and additionally as non-related nodes (indicated as a line of nodes, wherein the number of nodes was reduced for a better presentability). In this embodiment, the number of nodes 1018 in the fully connected layer 1008 is equal to the number of nodes 1016 in the preceding layer 1006. Alternatively, the number of nodes 1016, 1018 can differ.

Furthermore, in this embodiment, the values of the nodes 1020 of the output layer 1010 are determined by applying the Softmax function onto the values of the nodes 1018 of the preceding layer 1008. By applying the Softmax function, the sum the values of all nodes 1020 of the output layer 1010 is 1, and all values of all nodes 1020 of the output layer are real numbers between 0 and 1.

A convolutional neural network 1000 can also comprise a ReLU (rectified linear units) layer or activation layers with non-linear transfer functions. In particular, the number of nodes and the structure of the nodes contained in a ReLU layer is equivalent to the number of nodes and the structure of the nodes contained in the preceding layer. In particular, the value of each node in the ReLU layer is calculated by applying a rectifying function to the value of the corresponding node of the preceding layer.

The input and output of different convolutional neural network blocks can be wired using summation (residual/dense neural networks), element-wise multiplication (attention) or other differentiable operators. Therefore, the convolutional neural network architecture can be nested rather than being sequential if the whole pipeline is differentiable.

In particular, convolutional neural networks 1000 can be trained based on the backpropagation algorithm. For preventing overfitting, methods of regularization can be used, e.g. dropout of nodes 1012-1020, stochastic pooling, use of artificial data, weight decay based on the L1 or the L2 norm, or max norm constraints. Different loss functions can be combined for training the same neural network to reflect the joint training objectives. A subset of the neural network parameters can be excluded from optimization to retain the weights pretrained on another datasets.

Systems, apparatuses, and methods described herein may be implemented using digital circuitry, or using one or more computers using well-known computer processors, memory units, storage devices, computer software, and other components. Typically, a computer includes a processor for executing instructions and one or more memories for storing instructions and data. A computer may also include, or be coupled to, one or more mass storage devices, such as one or more magnetic disks, internal hard disks and removable disks, magneto-optical disks, optical disks, etc.

Systems, apparatus, and methods described herein may be implemented using computers operating in a client-server relationship. Typically, in such a system, the client computers are located remotely from the server computer and interact via a network. The client-server relationship may be defined and controlled by computer programs running on the respective client and server computers.

Systems, apparatus, and methods described herein may be implemented within a network-based cloud computing system. In such a network-based cloud computing system, a server or another processor that is connected to a network communicates with one or more client computers via a network. A client computer may communicate with the server via a network browser application residing and operating on the client computer, for example. A client computer may store data on the server and access the data via the network. A client computer may transmit requests for data, or requests for online services, to the server via the network. The server may perform requested services and provide data to the client computer(s). The server may also transmit data adapted to cause a client computer to perform a specified function, e.g., to perform a calculation, to display specified data on a screen, etc. For example, the server may transmit a request adapted to cause a client computer to perform one or more of the steps or functions of the methods and workflows described herein, including one or more of the steps or functions of FIGS. 1-4. Certain steps or functions of the methods and workflows described herein, including one or more of the steps or functions of FIGS. 1-4, may be performed by a server or by another processor in a network-based cloud-computing system. Certain steps or functions of the methods and workflows described herein, including one or more of the steps of FIGS. 1-4, may be performed by a client computer in a network-based cloud computing system. The steps or functions of the methods and workflows described herein, including one or more of the steps of FIGS. 1-4, may be performed by a server and/or by a client computer in a network-based cloud computing system, in any combination.

Systems, apparatus, and methods described herein may be implemented using a computer program product tangibly embodied in an information carrier, e.g., in a non-transitory machine-readable storage device, for execution by a programmable processor; and the method and workflow steps described herein, including one or more of the steps or functions of FIGS. 1-4, may be implemented using one or more computer programs that are executable by such a processor. A computer program is a set of computer program instructions that can be used, directly or indirectly, in a computer to perform a certain activity or bring about a certain result. A computer program can be written in any form of programming language, including compiled or interpreted languages, and it can be deployed in any form, including as a stand-alone program or as a module, component, subroutine, or other unit suitable for use in a computing environment.

Figure 11:
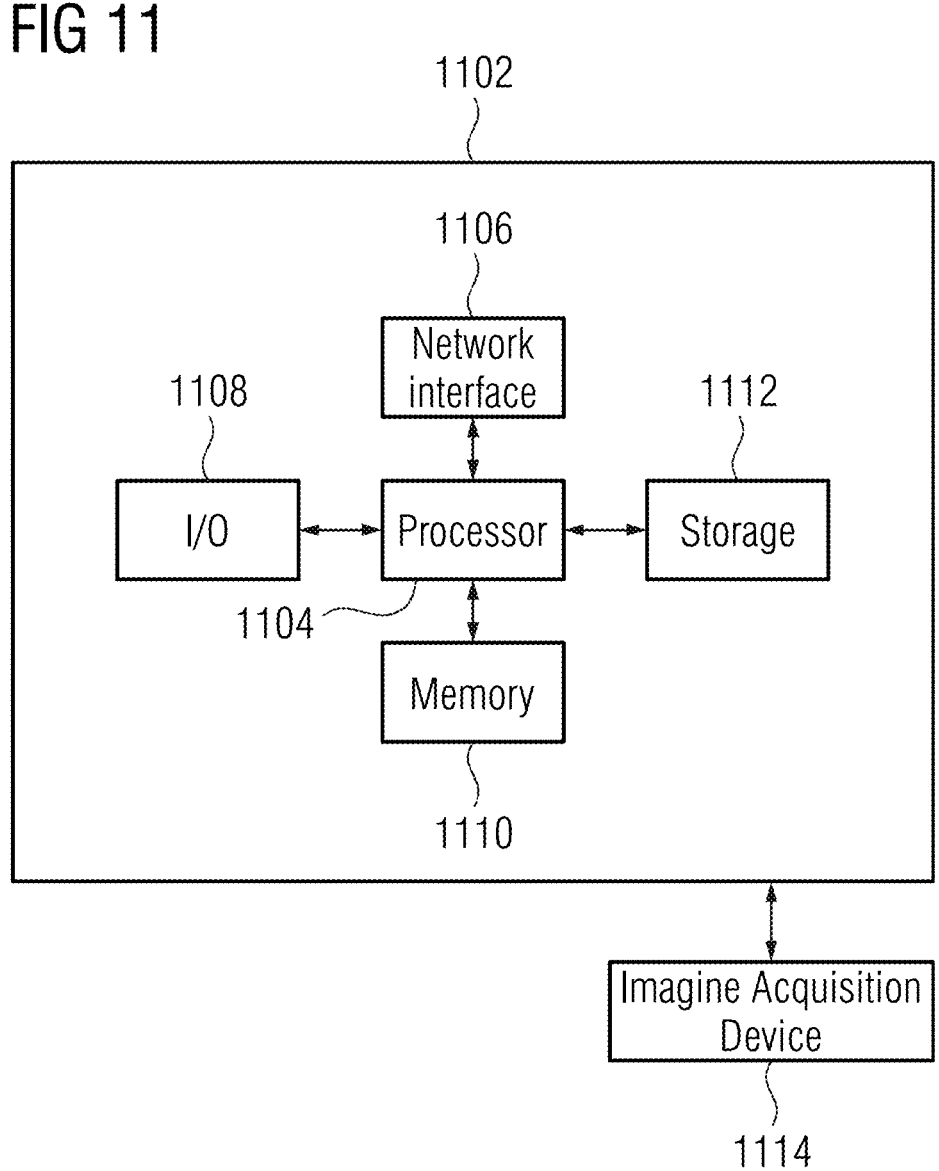
FIG. 11 shows a high-level block diagram of a computer that may be used to implement one or more embodiments.

A high-level block diagram of an example computer 1102 that may be used to implement systems, apparatus, and methods described herein is depicted in FIG. 11. Computer 1102 includes a processor 1104 operatively coupled to a data storage device 1112 and a memory 1110. Processor 1104 controls the overall operation of computer 1102 by executing computer program instructions that define such operations. The computer program instructions may be stored in data storage device 1112, or other computer readable medium, and loaded into memory 1110 when execution of the computer program instructions is desired. Thus, the method and workflow steps or functions of FIGS. 1-4 can be defined by the computer program instructions stored in memory 1110 and/or data storage device 1112 and controlled by processor 1104 executing the computer program instructions. For example, the computer program instructions can be implemented as computer executable code programmed by one skilled in the art to perform the method and workflow steps or functions of FIGS. 1-4. Accordingly, by executing the computer program instructions, the processor 1104 executes the method and workflow steps or functions of FIGS. 1-4. Computer 1102 may also include one or more network interfaces 1106 for communicating with other devices via a network. Computer 1102 may also include one or more input/output devices 1108 that enable user interaction with computer 1102 (e.g., display, keyboard, mouse, speakers, buttons, etc.).

Processor 1104 may include both general and special purpose microprocessors, and may be the sole processor or one of multiple processors of computer 1102. Processor 1104 may include one or more central processing units (CPUs), for example. Processor 1104, data storage device 1112, and/or memory 1110 may include, be supplemented by, or incorporated in, one or more application-specific integrated circuits (ASICs) and/or one or more field programmable gate arrays (FPGAs).

Data storage device 1112 and memory 1110 each include a tangible non-transitory computer readable storage medium. Data storage device 1112, and memory 1110, may each include high-speed random access memory, such as dynamic random access memory (DRAM), static random access memory (SRAM), double data rate synchronous dynamic random access memory (DDR RAM), or other random access solid state memory devices, and may include non-volatile memory, such as one or more magnetic disk storage devices such as internal hard disks and removable disks, magneto-optical disk storage devices, optical disk storage devices, flash memory devices, semiconductor memory devices, such as erasable programmable read-only memory (EPROM), electrically erasable programmable read-only memory (EEPROM), compact disc read-only memory (CD-ROM), digital versatile disc read-only memory (DVD-ROM) disks, or other non-volatile solid state storage devices.

Input/output devices 1108 may include peripherals, such as a printer, scanner, display screen, etc. For example, input/output devices 1108 may include a display device such as a cathode ray tube (CRT) or liquid crystal display (LCD) monitor for displaying information to the user, a keyboard, and a pointing device such as a mouse or a trackball by which the user can provide input to computer 1102.

An image acquisition device 1114 can be connected to the computer 1102 to input image data (e.g., medical images) to the computer 1102. It is possible to implement the image acquisition device 1114 and the computer 1102 as one device. It is also possible that the image acquisition device 1114 and the computer 1102 communicate wirelessly through a network. In a possible embodiment, the computer 1102 can be located remotely with respect to the image acquisition device 1114.

Any or all of the systems and apparatus discussed herein may be implemented using one or more computers such as computer 1102.

One skilled in the art will recognize that an implementation of an actual computer or computer system may have other structures and may contain other components as well, and that FIG. 11 is a high level representation of some of the components of such a computer for illustrative purposes.

Independent of the grammatical term usage, individuals with male, female or other gender identities are included within the term.

The foregoing Detailed Description is to be understood as being in every respect illustrative and exemplary, but not restrictive, and the scope of the invention disclosed herein is not to be determined from the Detailed Description, but rather from the claims as interpreted according to the full breadth permitted by the patent laws. It is to be understood that the embodiments shown and described herein are only illustrative of the principles of the present invention and that various modifications may be implemented by those skilled in the art without departing from the scope and spirit of the invention. Those skilled in the art could implement various other feature combinations without departing from the scope and spirit of the invention.

The invention claimed is:

1. A computer-implemented method comprising:
receiving 1) a 3D mask of an anatomical structure generated from a 3D medical image and 2) a 3D image of a plurality of concentric spheres;
generating a 3D mask of a tumor based on the 3D mask of the anatomical structure and the 3D image of the plurality of concentric spheres using a first 3D generator network;
generating a 3D intensity map of the tumor based on the 3D mask of the tumor and the 3D image of the plurality of concentric spheres using a second 3D generator network;
generating a 3D synthesized medical image of the tumor based on one or more 2D slices of the 3D intensity map of the tumor and one or more 2D slices of the 3D medical image using a 2D generator network; and
outputting the 3D synthesized medical image of the tumor.

2. The computer-implemented method of claim 1, further comprising:
smoothing the tumor in the 3D synthesized medical image using a 3D Gaussian kernel;
extracting the smoothed tumor from the 3D synthesized medical image; and
blending the extracted smoothed tumor with the 3D medical image.

3. The computer-implemented method of claim 2, further comprising:
adjusting a contrast of the extracted smoothed tumor.

4. The computer-implemented method of claim 1, wherein one or more of the first 3D generator network, the second 3D generator network, or the 2D generator network are trained based on at least one of 3D training images of a plurality of concentric spheres and 3D and 2D training intensity maps of a tumor, the 3D training images of the plurality of concentric spheres and the 3D and 2D training intensity maps of the tumor generated by:
receiving a 3D training image of the tumor and a 3D training mask of the tumor;
applying multi-Otsu thresholding to classify voxels of the 3D training image within the tumor identified in the 3D training mask to generate the 3D training intensity maps of the tumor;
generating the 3D training images of the plurality of concentric spheres based on a volume of the voxels in each of the classes in the 3D training intensity map of the tumor; and
generating the 2D training intensity map of the tumor by unstacking the 3D training intensity map of the tumor along an axis into 2D slices.

5. The computer-implemented method of claim 1, wherein the 2D generator network is trained with adversarial loss using a 2D discriminator network.

6. The computer-implemented method of claim 1, wherein the 2D generator network is trained with a 2D perceptual loss.

7. The computer-implemented method of claim 1, wherein the plurality of concentric spheres comprises three concentric spheres.

8. The computer-implemented method of claim 1, wherein the anatomical structure is a brain of a patient or a healthy subject.

9. The computer-implemented method of claim 1, further comprising:
   training a machine learning based network for performing a medical imaging analysis task based on the 3D synthesized medical image of the tumor.

10. An apparatus comprising:
   means for receiving 1) a 3D mask of an anatomical structure generated from a 3D medical image and 2) a 3D image of a plurality of concentric spheres;
   means for generating a 3D mask of a tumor based on the 3D mask of the anatomical structure and the 3D image of the plurality of concentric spheres using a first 3D generator network;
   means for generating a 3D intensity map of the tumor based on the 3D mask of the tumor and the 3D image of the plurality of concentric spheres using a second 3D generator network;
   means for generating a 3D synthesized medical image of the tumor based on one or more 2D slices of the 3D intensity map of the tumor and one or more 2D slices of the 3D medical image using a 2D generator network; and
   means for outputting the 3D synthesized medical image of the tumor.

11. The apparatus of claim 10, further comprising:
   means for smoothing the tumor in the 3D synthesized medical image using a 3D Gaussian kernel;
   means for extracting the smoothed tumor from the 3D synthesized medical image; and
   means for blending the extracted smoothed tumor with the 3D medical image.

12. The apparatus of claim 11, further comprising:
   means for adjusting a contrast of the extracted smoothed tumor.

13. The apparatus of claim 10, wherein one or more of the first 3D generator network, the second 3D generator network, or the 2D generator network are trained based on at least one of 3D training images of plurality of a concentric spheres and 3D and 2D training intensity maps of a tumor, the 3D training images of the plurality of concentric spheres and the 3D and 2D training intensity maps of the tumor generated by:
   means for receiving a 3D training image of the tumor and a 3D training mask of the tumor;
   means for applying multi-Otsu thresholding to classify voxels of the 3D training image within the tumor identified in the 3D training mask to generate the 3D training intensity maps of the tumor;
   means for generating the 3D training images of the plurality of concentric spheres based on a volume of the voxels in each of the classes in the 3D training intensity map of the tumor; and
   means for generating the 2D training intensity map of the tumor by unstacking the 3D training intensity map of the tumor along an axis into 2D slices.

14. The apparatus of claim 10, wherein the 2D generator network is trained with adversarial loss using a 2D discriminator network.

15. A non-transitory computer readable medium storing computer program instructions, the computer program instructions when executed by a processor cause the processor to perform operations comprising:
   receiving 1) a 3D mask of an anatomical structure generated from a 3D medical image and 2) a 3D image of a plurality of concentric spheres;
   generating a 3D mask of a tumor based on the 3D mask of the anatomical structure and the 3D image of the plurality of concentric spheres using a first 3D generator network;
   generating a 3D intensity map of the tumor based on the 3D mask of the tumor and the 3D image of the plurality of concentric spheres using a second 3D generator network;
   generating a 3D synthesized medical image of the tumor based on one or more 2D slices of the 3D intensity map of the tumor and one or more 2D slices of the 3D medical image using a 2D generator network; and
   outputting the 3D synthesized medical image of the tumor.

16. The non-transitory computer readable medium of claim 15, the operations further comprising:
   smoothing the tumor in the 3D synthesized medical image using a 3D Gaussian kernel;
   extracting the smoothed tumor from the 3D synthesized medical image; and
   blending the extracted smoothed tumor with the 3D medical image.

17. The non-transitory computer readable medium of claim 15, wherein the 2D generator network is trained with a 2D perceptual loss.

18. The non-transitory computer readable medium of claim 15, wherein the plurality of concentric spheres comprises three concentric spheres.

19. The non-transitory computer readable medium of claim 15, wherein the anatomical structure is a brain of a patient or healthy subject.

20. The non-transitory computer readable medium of claim 15, the operations further comprising:
   training a machine learning based network for performing a medical imaging analysis task based on the 3D synthesized medical image of the tumor.

* * * * *